United States Patent [19]

Eibl et al.

[11] Patent Number: 5,549,893
[45] Date of Patent: Aug. 27, 1996

[54] USE OF PROTEIN C IN THE TREATMENT OF PURPURA FULMINANS

[75] Inventors: Johann Eibl; Ludwig Pichler; Hans P. Schwarz, all of Vienna, Austria

[73] Assignee: Immuno Aktiengesellschaft, Vienna, Austria

[21] Appl. No.: 429,462

[22] Filed: Apr. 27, 1995

Related U.S. Application Data

[63] Continuation of Ser. No. 882,058, May 12, 1992, abandoned.

[30] Foreign Application Priority Data

May 14, 1991 [AT] Austria ........................... 991/91

[51] Int. Cl.⁶ ..................................... A61K 38/48
[52] U.S. Cl. ........................................ 424/94.64
[58] Field of Search ............................ 424/94.64

[56] References Cited

U.S. PATENT DOCUMENTS

| | | | |
|---|---|---|---|
| 5,009,889 | 4/1991 | Taylor et al. | 424/94.64 |
| 5,151,268 | 9/1992 | Baug et al. | 424/94.64 |

FOREIGN PATENT DOCUMENTS

| | | |
|---|---|---|
| 318201 | 5/1989 | European Pat. Off. |
| 0416890 | 3/1991 | European Pat. Off. |
| 471660 | 2/1992 | European Pat. Off. |
| WO90/08556 | 1/1990 | WIPO |
| 90/12028 | 10/1990 | WIPO |
| 90/09960 | 7/1991 | WIPO |

OTHER PUBLICATIONS

Alessandrescu et al., Rev. Roum. Morphol. Embryol. Physiol. Morphol. Embryol 26(1): 41–46 (1980).
Brozna, Seminars in Thrombosis & Hemostasis 16(4): 326–332 (1990).
Francis, Seminars in Thrombosis & Hemostasis 16(4):310–325 (1990).
Musher, Hospital Practice 24(5): 71–98 (May 15, 1989).
Fourrier et al., Intensive Care Med 16(2):121–124 (1990) Abstract BA:31449.
Taylor et al. (Apr. 1988) *Critical Care Medicine*, "Characterization of the Response to E. coli in the Baboon".
Taylor et al. (Mar. 1987) *J. Clin. Invest.* 79: 918–925, "Protein C Prevents the Coagulopathic and Lethal Effects of E. coli Infusion in the Baboon".
Schwartz et al. (Nov. 1990) *Blood Abstract No. 2070* 76: 7069, "Successful Treatment of Purpura and Longterm Therapy with a Highly Purified Protein C Concentrate".
Köhler et al. (Aug. 1975) *Nature* 266: 495–498, "Continuous Cultures of Fused Cells Secreting Antibody of Predefined Specificity".
D. Z. Chu, et al., "Purpura Fulminans", Medline Abstract No. 82157904, Am. J. Surg., Mar. 1982, 143(3), pp. 356–362.

*Primary Examiner*—Michael G. Wityshyn
*Assistant Examiner*—Jean C. Witz
*Attorney, Agent, or Firm*—Foley & Lardner

[57] ABSTRACT

There is disclosed the use of protein C or activated protein C for preparing a drug useful for the maintenance and improvement of the microcirculation in patients suffering from circulatory disturbances, in particular with the proviso that the drug does not contain any immunoglobulin G.

4 Claims, No Drawings

USE OF PROTEIN C IN THE TREATMENT OF PURPURA FULMINANS

This application is a continuation of application Ser. No. 07/882,058, filed May 12, 1992 now abandoned.

The invention relates to a new use of protein C or activated protein C for the preparation of a drug.

Protein C is a vitamin K-dependent glycoprotein that is synthesized in the liver and circulates in plasma as an inactive zymogen at a concentration of 4 µg/ml. It is converted into the active serine protease (activated protein C) by the thrombin-thrombomodulin complex on the surface of the vessel wall (endothelium). It is known that activated protein C has profibrinolytic properties. It also has an anticoagulant effect, because it proteolytically degrades both factor Va, the cofactor for the factor Xa-induced prothrombin activation (thrombin formation), and factor VIIIa, the cofactor for the factor IXa-induced factor X activation.

The activation of protein C in vivo constitutes a negative feedback reaction in the generation of thrombin. A process for the preparation of activated protein C in vitro is described, for instance, in EP-A- 0 416 890.

It is known that activated protein C has a favorable effect on sepsis and septic shock.

Septic shock is the systemic reaction to the release of endotoxins, i.e., lipopolysaccharide components of the cell walls of gram negative bacteria, into the circulation. Septic shock is a major cause of death of hospitalized patients. Frequently, gram negative bacteremia proves to be the cause of sepsis.

Septic shock and the Shwartzman reaction show comparable pathophysiologic elements. The Shwartzman reaction is an inflammatory hemorrhagic and thrombotically necrotizing lesion of the skin elicited by the local and subsequent intravenous administration of endotoxin of gram negative bacteria. Specific syndromes in man, which are described in the following, are to be attributed to the Shwartzman reaction.

A skin lesion macroscopically occurring in the Shwartzman reaction very much resembles the syndrome of purpura fulminans in septic conditions (e.g., meningococcus sepsis). Purpura fulminans is a potentially fatal syndrome that induces extensive skin necroses and autoamputations of the extremities. Despite conventional therapeutical attempts, for example, by means of antibiotics or intensive care procedure, the death rate is very high.

Likewise, chronic ulcerative diseases of the intestines constitute an example of the Shwartzman reaction in man. Again, circulating endotoxins induce the infection of the wall of the intestines, a local lesion corresponding to the Shwartzman reaction.

The effects of septic shock elicited by an infection with *E. coli* in baboons are summarized in Critical Care Medicine (1988). Primarily, an inflammatory reaction is caused and, secondarily, coagulopathic reactions and cell injury occur. It is mentioned that the infusion of activated protein C protects against the secondary consequences of the infection.

In PCT application WO 90/08556, combined preparations for the treatment and prophylaxis of sepsis and septic shock are described, which comprise a bactericidal effective amount of immunoglobulin G as well as a blood clot-dissolving effective amount of activated protein C. It is recommended not to use the zymogen protein C because of potential difficulties with in vivo activation.

Likewise, it is known from J. Clin. Invest. (1987) that the effect of an infection with *E. coli* in baboons will be aggravated by blocking in vivo protein C activation. This even leads to the death of the test animals in case of infections with sublethal doses of *E. coli*. However, the death may be prevented by coinfusion of activated protein C. Nothing is said about a preventive or therapeutic effect of the zymogen.

Furthermore, it is known that many patients suffering from protein C deficiency exhibit purpura fulminans syndrome, which has been successfully treated with a protein C concentrate (Blood 10, Suppl. 1: 2070, 1990). However, the triggering mechanism of this disease substantially differs from purpura fulminans elicited by a microbial infection. Equivalent treatment would therefore not be an obvious option in the case of sepsis.

In addition to purpura fulminans, dermatitis ulcerosa also may be induced by endotoxins. So far, no remedy has been known for the prophylaxis and therapy of these syndromes.

It is the object of the invention to widen the field of therapeutic application of protein C or activated protein C.

The invention consists in the use of protein C or activated protein C for the preparation of a drug intended for the maintenance and improvement of microcirculation in patients suffering from circulatory disturbances, as well as for the prophylaxis and therapy of the clinical equivalents to the local and generalized Shwartzman reactions, in particular, with the proviso that the drug does not contain any immunoglobulin G. Both protein C and activated protein C have proved to exhibit excellent activities in the above-mentioned cases without being combined with bactericidal effective substances.

Protein C or activated protein C has proved particularly useful for the treatment of circulatory disturbances associated with malign diseases, autoimmune diseases, immunocomplex diseases, infectious diseases and with shock syndromes.

Other preferred indications are:

reduction of inflammatory processes caused by an impaired microcirculation;

prophylaxis and therapy of purpura fulminans caused by microbial infections; and prophylaxis and therapy of clinical equivalents to local and generalized Shwartzman reactions.

In the same manner, protein C, according to the invention, may be used for the preparation of drugs intended for the prophylaxis and therapy of chronic inflammatory diseases of the intestines and for the prophylaxis and therapy of dermatitis ulcerosa.

It was demonstrated in an animal model that both the zymogen protein C and activated protein C attenuate the local Shwartzman reaction. The therapeutic mechanism is presumed to be associated with the inhibition of the stimulation of leukocytes and of the synthesis and release of cytokins caused by endotoxin. In addition, it is assumed that the endothelial stimulation and expression of leukocyte adhesion molecules are prevented and leukocytic adhesion is suppressed. It was demonstrated that protein C or activated protein C prevents the microcirculatory clot-forming activation and thrombosis elicited by microbiologic infections.

The preparation of protein C and of activated protein C as well as the investigation as to their influence on the local Shwartzman reaction will be described in the following.

Preparation of Protein C

Highly purified protein C was recovered from a crude protein C fraction obtained from commercially available prothrombin complex concentrate. Purification was effected by affinity chromatography by means of monoclonal antibodies. Monoclonal anti-protein C antibodies were produced as follows:

BALB/C mice were immunized with 100 µg human protein C by intraperitoneal injection at two-week intervals. After six weeks, another 50 µg of human protein C were injected and fusion was carried out three days later. The myeloma cell line (P3-X-63-AG8- 653, 1.5×10$^7$ cells) was mixed with 1.7×10$^8$ mouse spleen cells and fused according to the modified method of Köhler & Milestein by using PEG 1500 (Köhler G., Milestein C., Nature 256 (1975), 495–497).

Positive clones, assayed by means of ELISA, were subcloned twice. Ascites production was effected by injection of 5×10$^6$ hybridoma cells per BALB/C mouse two weeks after Pristan treatment.

The immunoglobulin was purified from ascites by means of ammonia sulfate precipitation and subsequent chromatography on QAE-Sephadex (Pharmacia) and, further, by chromatography on Sephadex G200 (Pharmacia). To reduce the risk of transmission of murine viruses, the antibody was subjected to a further virus inactivation step prior to immobilization. The monoclonal protein C antibodies thus obtained were coupled to CNBr-activated Sepharose 4B (Pharmacia). The following buffers were used for the purification of protein C by means of affinity chromatography:

Adsorption buffer: 20 mM Tris, 2 mM EDTA, 0.25 mM NaCl and 5 mM benzamidine;

Washing buffer: 20 mM Tris, 1M NaCl, 2 mM benzamidine, 2 mM EDTA, pH 7.4;

Elution buffer: 3M NaSCN, 20 mM Tris, 1M NaCl, 0.5 mM benzamidine, 2 mM EDTA.

In detail: The prothrombin complex concentrate was dissolved in the adsorption buffer, with approximately 10 g of the prothrombin complex concentrate being employed for a 20 ml monoclonal antibody column. Subsequently, the dissolved prothrombin complex concentrate was filtered, centrifuged at 20,000 r.p.m. for 15 min and sterile filtered through a 0.8 µm filter. The sterile filtered and dissolved prothrombin complex concentrate was applied to the column at a flow rate of 10 ml/h. Subsequently, the column was washed free of non-bound protein with the washing buffer, and finally the bound protein C was eluted by means of the elution buffer at a flow rate of 5 ml/h and the fractions were collected. The eluted protein C was dialyzed against a buffer (0.2 mol/l Tris, 0.15M glycine and 1 mM EDTA, pH 8.3). Protein C antigen concentration was determined using the method described by Laurell, and protein C activity was determined using Protac activation.

The protein C eluate thus obtained was then finished to a pharmaceutically applicable preparation in the following manner:

The eluate was first subjected to ultrafiltration and diafiltration steps. Diafiltration was carried out with a buffer containing 150 mmol NaCl and 15 mmol trisodium citrate.2H$_2$O per liter, at a pH of 7.4. The obtained filtrate was then freeze-dried and virus inactivated by a one-hour vapor treatment at 80° C.±5° C. and at 1375±35 mbar.

The lyophilized, virus inactivated material was then dissolved in a sterile isotonic NaCl solution and potentially present antibodies or serum amyloid P were eliminated by means of ion exchange chromatography on Q-Sepharose® (Pharmacia). The purified solution was concentrated by means of an additional ultrafiltration and diafiltration stage. After this stage, 10 g albumin, 150 mmol NaCl and 15 mmol trisodium citrate per liter were added to the solution obtained. The pH of the solution was 7.5. Neither murine immunoglobulin nor factors II, VII, IX and X could be detected. Subsequently, the solution was sterile filtered, filled in containers and lyophilized. The specific activity was 14 units protein C per mg of protein. One unit of protein C activity is defined as the protein C activity in 1 ml normal plasma and is calibrated against the first international standard of protein C. An amidolytic assay was used as the activity test, wherein protein C is activated by means of Protac (from Pentapharm).

Preparation of Activated Protein C

Activation of the purified protein C was effected by coupling 70 ml thrombin (500 NIH units/ml corresponding to approximately 2000 NIH units/mg protein) to CNBr-activated Sepharose 4 B (Pharmacia), whereupon protein C was mixed with the thrombin gel at a ratio of about 6 units protein C to 1 unit thrombin at 37° C. and allowed to react for 3 hours under continuous shaking. The protein C activity was then determined by means of chromogenic substrate (S 2366). The activated protein C subsequently was sterile filtered and finished to a pharmaceutical preparation as described above.

Influence on the Local Shwartzman Reaction in Rabbit by Protein C

Method: The assays were carried out in (White New Zealand) rabbits of both sexes weighing 2 to 3 kg.

Under brief anesthesia (20 mg/kg Ketamin®+5 mg/kg Rombun® i.m.), the abdominal skin of rabbits was depilated by shaving and by using Depilan®. After this, six wheals were intradermally raised in each animal with 0.2 ml endotoxin of Salmonella typhimurium (Sigma L 7261) each. The endotoxin doses employed were 6.25, 12.5, 25, 50, 100 and 200 µg (preparative doses). 24 hours later, the rabbits received 20 µg/kg of the endotoxin i.v. in an ear vein (0.2 ml/kg; provocative dose.

There were assayed:

A) Activated protein C (n=5 animals) intravenously according to the following scheme: 250 U/kg immediately upon the provocative dose and 50 U/kg after 1, 2 and 3 hours each. The injection volume was 0.25 ml/50 U.

B) Protein C (n=7 animals), 500 U/kg i.v. immediately upon the provocative dose and 100 U/kg after 1, 2 and 3 hours each. The injection volume was 0.8 ml/100 U.

C) A separate control group (n=6 and 5 animals, respectively) was established for each assayed group (A, B). Apart from the preparative endotoxin doses and the provocative dose, these animals received no other treatment.

The assessment of the changes of the skin took place 6, 24 and 48 hours after the provocative dose. The parameters "thickening and swelling" (0–3), "size" (0–4), "color" (0–4) and "ring formation" (0–1) were assessed (the numbers in parentheses indicate the scores by aid of which each individual parameter was quantified). The scores of the individual parameters were added to a total score characterizing the extent of the respective change of the skin.

From the total scores of each dose group, the mean values were calculated both for the animals of the assayed groups and for the control animals and are depicted in the Table. These results are based on 6-hour values.

Results: Lesions of the skin were observed, reaching from petechial rubor to high-grade intradermal hemorrhage with surface crust formation. The degree of the skin lesions depended on the dose of the preparative toxin injection and on the treatment with the test substances. As is apparent from the Table, the changes in untreated control animals are severe, while those of treated rabbits (activated protein C, protein C) are only moderate.

TABLE

Shwartzman Reaction in Rabbit

| Treatment group | n | Skin lesion, score (mean value), on the sites of preparative toxin injection (μg) | | | | | |
|---|---|---|---|---|---|---|---|
| | | 6.25 | 12.5 | 25 | 50 | 100 | 200 |
| A | 5 | 0.4 | 0.2 | 2.8 | 4.6 | 5.0 | 5.8 |
| $C_A$ | 6 | 2.5 | 4.7 | 5.4 | 8.3 | 8.7 | 9.7 |
| B | 7 | 1.0 | 1.1 | 2.0 | 3.3 | 3.6 | 5.4 |
| $C_B$ | 5 | 1.2 | 2.2 | 4.8 | 7.0 | 7.8 | 8.4 |

Activated protein C (400 U/kg i.v.) and protein C (800 U/kg i.v.) may be compared as to their protective effects illustrated. If the mean values of the scores (cf. Table) are plotted against the doses on a logarithmic scale, parallel dose-response curves will result.

Pretreatment with activated protein C and with protein C shift the dose-response curves established for the respective controls to the right each by a factor 4, towards higher doses.

What we claim is:

1. A method for the prophylaxis of purpura fulminans in a patient exposed to endotoxin, comprising the step of administering to said patient an effective amount of a concentrate of non-activated protein C.

2. A method according to claim 1, wherein said concentrate does not contain IgG.

3. A method of treating purpura fulminans in a patient exposed to endotoxin, comprising the step of administering to said patient an effective amount of a concentrate of non-activated protein C.

4. A method according to claim 3, wherein said concentrate does not contain IgG.

* * * * *